(12) United States Patent
Ahn et al.

(10) Patent No.: US 10,413,579 B2
(45) Date of Patent: Sep. 17, 2019

(54) **PHARMACEUTICAL COMPOSITION FOR PREVENTING OR TREATING ASTHMA COMPRISING *PISTACIA WEINMANNIFOLIA* J. POISS. EX FRANCH EXTRACT OR FRACTION THEREOF**

(71) Applicant: Korea Research Institute of Bioscience and Biotechnology, Daejeon (KR)

(72) Inventors: Kyung Seop Ahn, Daejeon (KR); Sei Ryang Oh, Daejeon (KR); Ok Kyoung Kwon, Daejeon (KR); In Sik Shin, Daejeon (KR); Hyung Won Ryu, Daejeon (KR); Sang Woo Lee, Daejeon (KR); Joong Ku Lee, Daejeon (KR); Hyeong Kyu Lee, Daejeon (KR); Sang Ho Choi, Daejeon (KR); Doo Young Kim, Daejeon (KR); Jung Hee Kim, Daejeon (KR); Li Wan Yi, Kunming (CN); Jin Hang, Kunming (CN)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 665 days.

(21) Appl. No.: 14/902,439

(22) PCT Filed: Jul. 1, 2014

(86) PCT No.: PCT/KR2014/005844
§ 371 (c)(1),
(2) Date: Feb. 6, 2017

(87) PCT Pub. No.: WO2015/002430
PCT Pub. Date: Jan. 8, 2015

(65) Prior Publication Data
US 2017/0173095 A1 Jun. 22, 2017

(30) Foreign Application Priority Data
Jul. 1, 2013 (KR) .................. 10-2013-0076696

(51) Int. Cl.
*A61K 36/22* (2006.01)
*A23L 33/105* (2016.01)

(52) U.S. Cl.
CPC ............ *A61K 36/22* (2013.01); *A23L 33/105* (2016.08); *A23V 2002/00* (2013.01); *A61K 2236/33* (2013.01)

(58) Field of Classification Search
None
See application file for complete search history.

(56) References Cited

U.S. PATENT DOCUMENTS

| 2003/0096020 A1 | 5/2003 | Brindavanam et al. |
| 2004/0161477 A1 | 8/2004 | Wagner et al. |

FOREIGN PATENT DOCUMENTS

| JP | 2004/262905 A | 9/2004 |
| JP | 2004262905 A | * 9/2004 |

OTHER PUBLICATIONS

Balfour, E. "Pistachia" from The Cyclopaedia of India and of Eastern and Southern Asia. p. 226. (Year: 1995).*
The Plant List (2010). Version 1. Published on the Internet; http://www.theplantlist.org/ (accessed Oct. 1, 2018). (Year: 2010).*
Kim, S.-H et al., "Gallic acid inhibits histamine release and proinflammatory cytokine production in mast cells", Toxicological Sciences, 2006, 123-131p.
Minami, K. et al. Isolation and identification of histamine-release inhibitors form Pistacia weinmannifolia J. Pisson ex. Franch J. Nat. Med., 138-140p, 2006.
Zhao X. et al., Biochim Biophys Acta, 1725, 103-110, 2005.
Shirole et al "Investigation into the Mechanism of Action of Essential Oil of Pistacia Integerrima for its Antiasthmatic Activity" Journal of Ethnopharmacology vol. 153, pp. 541-551, 2014.

* cited by examiner

*Primary Examiner* — Amy L Clark
(74) *Attorney, Agent, or Firm* — Cesari & McKenna, LLP (57) ABSTRACT

The present invention relates to a composition for preventing or treating asthma comprising a *Pistacia weinmannifolia* J. Poiss. ex Franch extract or a fraction thereof. The *Pistacia weinmannifolia* J. Poiss. ex Franch extract or the fraction thereof according to the present invention does not exhibit toxicity, inhibits the generation of NO, IL-4, IL-5, and IL-13 and the generation of reactive oxygen species in the bronchial tubes, and has significantly induced the alleviation of airway hyperresponsiveness, inhibition of the infiltration of inflammatory cells into the bronchial tubes, and reduction of inflammatory cells in bronchoalveolar lavage fluid in an ovalbumin-induced asthma mouse model. In addition, the *Pistacia weinmannifolia* J. Poiss. ex Franch extract or the fraction thereof according to the present invention effectively inhibits the secretion of immunoglobulins in serum, secretion of mucus in the bronchial tubes, and infiltration of inflammatory cells into lung tissue and thus can be usefully used as a safe preparation for preventing and treating asthma.

9 Claims, 8 Drawing Sheets

PHARMACEUTICAL COMPOSITION FOR PREVENTING OR TREATING ASTHMA COMPRISING *PISTACIA WEINMANNIFOLIA* J. POISS. EX FRANCH EXTRACT OR FRACTION THEREOF

CROSS REFERENCE TO RELATED APPLICATIONS

This application is a National Stage Entry of PCT/KR2014/005844, filed Jul. 1, 2014, which claims the benefit of Korean Application No. 10-2013-0076696, filed Jul. 1, 2013. The contents of said applications are incorporated herein by reference for all purposes.

BACKGROUND OF THE INVENTION

1. Field of the Invention

The present disclosure relates to a pharmaceutical composition for preventing or treating asthma including a *Pistacia weinmannifolia* (*Pistacia weinmannifolia* J. Poiss. Ex Franch) extract or a fraction thereof as an active ingredient, a health functional food for preventing or improving asthma including the extract or the fraction thereof, and use of the extract or the fraction thereof for the prevention or treatment of asthma.

2. Description of the Related Art

Asthma is a respiratory disease that causes difficulty in breathing, and about 3 million peoples of the Korean population suffer from asthma. Asthma is a disease accompanied by stridor, difficulty in breathing, sneezing, and cyanosis and chest pain due to a lack of oxygen in severe case. Recently, incidence of asthma is rapidly increasing due to air pollution, exposure to various chemicals, and westernized diets, and particularly, prevalence of asthma in children is increasing.

Asthma is a disease caused by $TH_2$ (T-helper2) type-driven immune responses, which release interleukin-4, 5, 13, leading to recruitment and infiltration of a variety of inflammatory cells including eosinophils to the airways and tissues surrounding blood vessels. Various inflammatory mediators produced therefrom further increase inflammatory responses, resulting in an increase in mucus secretion and airway hyperresponsiveness.

With recent development of molecular biology, many attempts have been made to understand the roles of cytokines in asthma at a molecular level, and factors that influence this disease have been demonstrated one by one. Among the factors, nitric oxide (NO) is an inflammatory mediator, which acts as a defense by damaging pathogenic DNA, thereby maintaining homeostasis. NO is produced from L-arginine by three main isoforms of nitric oxide synthase (NOS), named nNOS (neuronal NOS), eNOS (endothelial NOS), and iNOS (inducible NOS). Excessive production of NO by iNOS of the isoforms is involved in various pathophysiological processes, including inflammation and cancer.

Until now, there have been developed many therapeutic agents for the treatment of asthma, such as steroids, bronchodilators, anti-inflammatory drugs, etc., but most of the therapeutic agents cause a wide range of side effects and thus use of the agents needs careful management. The most widely used inhaled corticosteroids exhibit excellent therapeutic effects, but long-term use thereof is known to cause adrenal suppression, reduction in bone density, growth retardation, complications in the eyes and skin, and increase in collagen synthesis, in proportion to the dose and period of use. Further, long-acting beta-2 agonists such as salmeterol and formoterol exhibit and prophylactic effect on asthma attack, but possibly leading to death in some patients. Due to such various side effects, careful consideration should be given to use of the existing asthma therapeutic agents. There is a continuous demand to develop a prophylactic or therapeutic agent for asthma with strong efficacy and fewer side effects.

Meanwhile, *Pistacia weinmannifolia* (*Pistacia weinmannifolia* J. Poiss, Ex Franch) is a plant widely found in Yunnan province of China and traditionally, it has been used in dysentery, enteritis, influenza, or headache. A previous research reported that two compounds isolated from this plant have a reactive oxygen species-scavenging ability (Zhao X. et al., Biochim Biophys Acta, 1725, 103-110, 2005). Besides this report, there is no report about an anti-asthma effect of a *Pistacia weinmannifolia* extract, a fraction thereof, or a compound isolated therefrom.

The present inventors have made many efforts to find out natural substances which are useful for the prevention or treatment of asthma without causing side effects in human, and as a result, they found that a *Pistacia weinmannifolia* extract or a fraction thereof suppresses nitric oxide production in animal cells, alleviates airway hyperresponsiveness in asthma-induced mouse models, and inhibits generation of reactive oxygen species in the airway without toxicity. The present inventors also found that the *Pistacia weinmannifolia* extract or the fraction thereof reduces the number of inflammatory cells and the level of interleukin in bronchoalveolar lavage fluid, inhibits IgE production in the serum and infiltration of inflammatory cells to the lung tissue, and reduces mucus secretion in the airway, and therefore, it is useful for the prevention or treatment of asthma, thereby completing the present invention.

SUMMARY OF THE INVENTION

An object of the present invention is to provide a pharmaceutical composition for preventing or treating asthma, the composition including a *Pistacia weinmannifolia* (*Pistacia weinmannifolia* J. Poiss. Ex Franch) extract or a fraction thereof as an active ingredient.

Another object of the present invention is to provide a health functional food composition for preventing or improving asthma, the composition including the *Pistacia weinmannifolia* extract or the fraction thereof.

Still another object of the present invention is to provide use of the *Pistacia weinmannifolia* extract or the fraction thereof in the preparation of a medicament for preventing or treating asthma.

Still another object of the present invention is to provide a method of treating asthma, the method including administering the pharmaceutical composition to a subject suspected of having asthma.

BRIEF DESCRIPTION OF THE DRAWINGS

EA5: Experimental group administered with Active fraction 5 of ethyl acetate fraction of *Pistacia weinmannifolia*

EA6: Experimental group administered with Active fraction 6 of ethyl acetate fraction of *Pistacia weinmannifolia*

Hex7: Experimental group administered with Active fraction 7 of hexane fraction of *Pistacia weinmannifolia*

\#: considered statistically significant, compared to the normal control group (NC) ($p<0.05$)

*: considered statistically significant, compared to the asthma-induced group (OVA) ($p<0.05$).

EA5: Experimental group administered with Active fraction 5 of ethyl acetate fraction of *Pistacia weinmannifolia*

EA6: Experimental group administered with Active fraction 6 of ethyl acetate fraction of *Pistacia weinmannifolia*

Hex7: Experimental group administered with Active fraction 7 of hexane fraction of *Pistacia weinmannifolia*

\#: considered statistically significant, compared to the normal control group (NC) ($p<0.05$)

*: considered statistically significant, compared to the asthma-induced group (OVA) ($p<0.05$).

EA5: Experimental group administered with Active fraction 5 of ethyl acetate fraction of *Pistacia weinmannifolia*

EA6: Experimental group administered with Active fraction 6 of ethyl acetate fraction of *Pistacia weinmannifolia*

Hex7: Experimental group administered with Active fraction 7 of hexane fraction of *Pistacia weinmannifolia*.

EA5: Experimental group administered with Active fraction 5 of ethyl acetate fraction of *Pistacia weinmannifolia*

EA6: Experimental group administered with Active fraction 6 of ethyl acetate fraction of *Pistacia weinmannifolia*

Hex7: Experimental group administered with Active fraction 7 of hexane fraction of *Pistacia weinmannifolia*.

EA5: Experimental group administered with Active fraction 5 of ethyl acetate fraction of *Pistacia weinmannifolia*

EA6: Experimental group administered with Active fraction 6 of ethyl acetate fraction of *Pistacia weinmannifolia*

Hex7: Experimental group administered with Active fraction 7 of hexane fraction of *Pistacia weinmannifolia*.

DETAILED DESCRIPTION OF THE PREFERRED EMBODIMENTS

In an aspect, the present invention provides a pharmaceutical composition for preventing or treating asthma, the composition including a *Pistacia weinmannifolia* extract or a fraction thereof as an active ingredient.

With respect to the object of the present invention, the *Pistacia weinmannifolia* extract or the fraction thereof according to the present invention is used for preventing or treating asthma.

As used herein, the term "*Pistacia weinmannifolia* (*Pistacia weinmannifolia* J Poiss, Ex Franch)" is a plant widely found in Yunnan province of China and traditionally, it has been used in dysentery, enteritis, influenza, or headache. However, there has been no report about an anti-asthma effect of the *Pistacia weinmannifolia* extract, the fraction thereof, or compounds isolated therefrom.

As used herein, the term "*Pistacia weinmannifolia* extract" refers to an extract obtained by extracting *Pistacia weinmannifolia* using a proper solvent. In the present invention, the *Pistacia weinmannifolia* extract may include any one or more of a liquid extract obtained by extracting *Pistacia weinmannifolia* using proper solvent, a diluted or concentrated liquid of the liquid extract, a dried product obtained by drying the liquid extract, and a crude purification product or a purification product thereof.

The *Pistacia weinmannifolia* extract of the present invention may be prepared by an extraction method generally used in the art, such as a sonication extraction method, a filtration method, and a reflux extraction method, and *Pistacia weinmannifolia* may be purchased from a commercially available source, or collected from or grown in nature.

Further, any part of *Pistacia weinmannifolia*, for example, stem may be used without particular limitation, as long as it exhibits anti-asthma efficacy.

The *Pistacia weinmannifolia* extract according to the present invention may be separated according to a general method of preparing an extract from a natural substance, which is known in the art, that is, by using a general solvent under conditions of general temperature and pressure.

In the preparation of the *Pistacia weinmannifolia* extract according to the present invention, water anhydrous or water-containing C1~C4 lower alcohols, or a mixed solvent thereof may be used, but is not limited thereto. Specifically, methanol or ethanol may be used to prepare the *Pistacia weinmannifolia* extract.

According to a specific embodiment of the present invention, in the preparation of the *Pistacia weinmannifolia* extract, the stems of collected *Pistacia weinmannifolia* are first dried and then pulverized. 2 to 20 times volume of ethanol is added to the pulverized powder sample, based on the dry weight thereof, and then extraction may be performed at 20 to 30° C., specifically, at room temperature for 5 to 15 days, more specifically, for 10 days. Subsequently, filtration and concentration under reduced pressure are performed to obtain an ethanol extract of *Pistacia weinmannifolia*. This extraction process may be repeated 2 to 3 times, and a process of filtration, concentration, freeze-drying, etc. may be further performed.

As used herein, the term "fraction" refers to a product obtained by a fractionation method of separating a particular component or a particular group from the *Pistacia weinmannifolia* extract thus prepared.

In order to obtain the *Pistacia weinmannifolia* fraction according to the present invention, a general fractionation solvent known in the art, for example, a polar solvent including water, or anhydrous or water-containing C1~C4 lower alcohols such as ethanol or methanol, etc., a non-polar solvent such as hexane, ethyl acetate, chloroform, dichloromethane, etc., or a mixed solvent thereof may be used, but is not limited thereto.

The *Pistacia weinmannifolia* fraction of the present invention may include products obtained by further applying a purification process. Fractions obtained through various additional purification methods, for example, separation by passing the *Pistacia weinmannifolia* extract according to the present invention through an ultrafiltration membrane having a given molecular weight cut-off, or separation by various chromatography systems (manufactured for separation according to size, charge, hydrophobicity or affinity), may be also included in the *Pistacia weinmannifolia* fraction of the present invention.

In a specific embodiment of the present invention, the obtained ethanol extract of *Pistacia weinmannifolia* is suspended in distilled water, and an equal amount of hexane is added to separate a hexane layer and an aqueous layer. This procedure is repeated three times, followed by filtration and concentration under reduced pressure to obtain a hexane fraction. Thereafter, the hexane fraction is removed, and to the remaining aqueous layer, an equal amount of chloroform is added to obtain a chloroform fraction in the same manner. To the remaining aqueous layer, an equal amount of ethyl acetate is added to obtain an ethyl acetate fraction in the same manner. To the aqueous layer obtained therefrom, an equal amount of butanol is added to obtain a butanol fraction in the same manner.

In a specific embodiment of the present invention, the therapeutic effects of the *Pistacia weinmannifolia* extract and the fractions thereof thus obtained on asthma were examined. As a result, the ethanol extract, the hexane fraction, and the ethyl acetate fraction of *Pistacia weinmannifolia* according to the present invention were found to remarkably reduce production of nitric oxide in LPS-treated macrophages (see FIGS. 3a to 3c), and to reduce airway hyperresponsiveness caused by an increase in a methacholine concentration (see FIG. 4).

Figure 5:
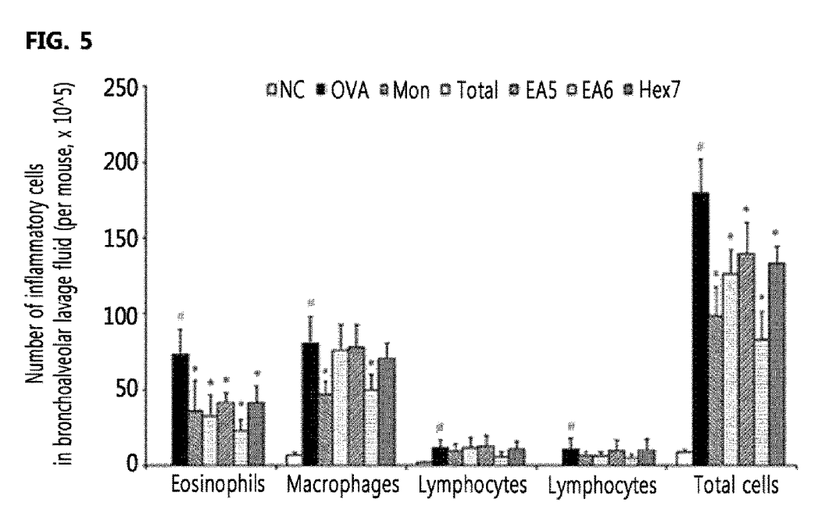
FIG. 5 shows the result of measuring effects of the total extract, hexane fraction and ethyl acetate fraction of *Pistacia weinmannifolia* on the numbers of eosinophils, macrophages, lymphocytes, neutrophils and total cells in bronchoalveolar lavage fluid in ovalbumin-sensitized asthma animal models, NC: Normal control group whose airway was not sensitized OVA: Asthma-induced group whose airway was sensitized with ovalbumin Mon: Comparative group administered with montelukast Total: Experimental group administered with ethanol extract of *Pistacia weinmannifolia*
Figure 6:
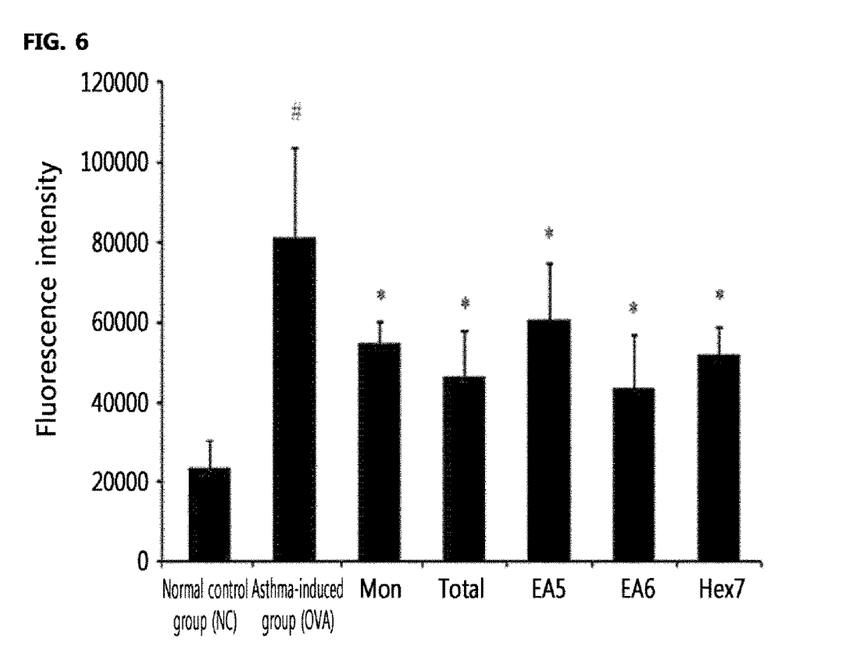
FIG. 6 shows the result of measuring effects of the total extract, hexane fraction and ethyl acetate fraction of *Pistacia weinmannifolia* on generation of reactive oxygen species in ovalbumin-sensitized asthma animal models, NC: Normal control group whose airway was not sensitized OVA: Asthma-induced group whose airway was sensitized with ovalbumin Mon: Comparative group administered with montelukast Total: Experimental group administered with ethanol extract of *Pistacia weinmannifolia*

In a specific embodiment of the present invention, the ethanol extract, the hexane fraction, and the ethyl acetate fraction of *Pistacia weinmannifolia* according to the present invention were also found to remarkably reduce the number of inflammatory cells in bronchoalveolar lavage fluid (see FIG. 5), to remarkably reduce an IgE antibody level in the serum and an ovalbumin-specific IgE antibody level (see Table 1), and to effectively inhibit generation of reactive oxygen species (see FIG. 6).

Figure 7:
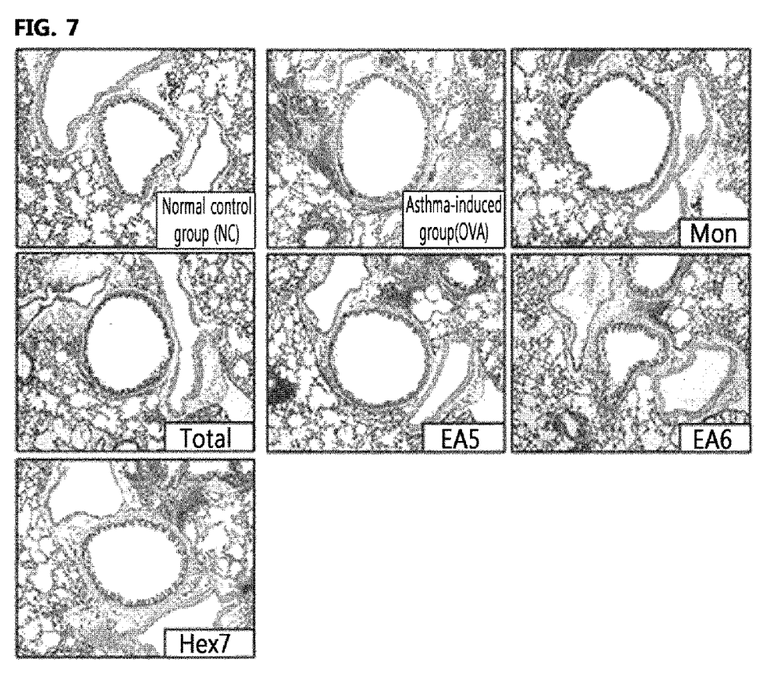
FIG. 7 shows the result of measuring effects of the total extract, hexane fraction and ethyl acetate fraction of *Pistacia weinmannifolia* on infiltration of inflammatory cells in ovalbumin-sensitized asthma animal models, NC: Normal control group whose airway was not sensitized OVA: Asthma-induced group whose airway was sensitized with ovalbumin Mon: Comparative group administered with montelukast Total: experimental group administered with ethanol extract of *Pistacia weinmannifolia*
Figure 8:
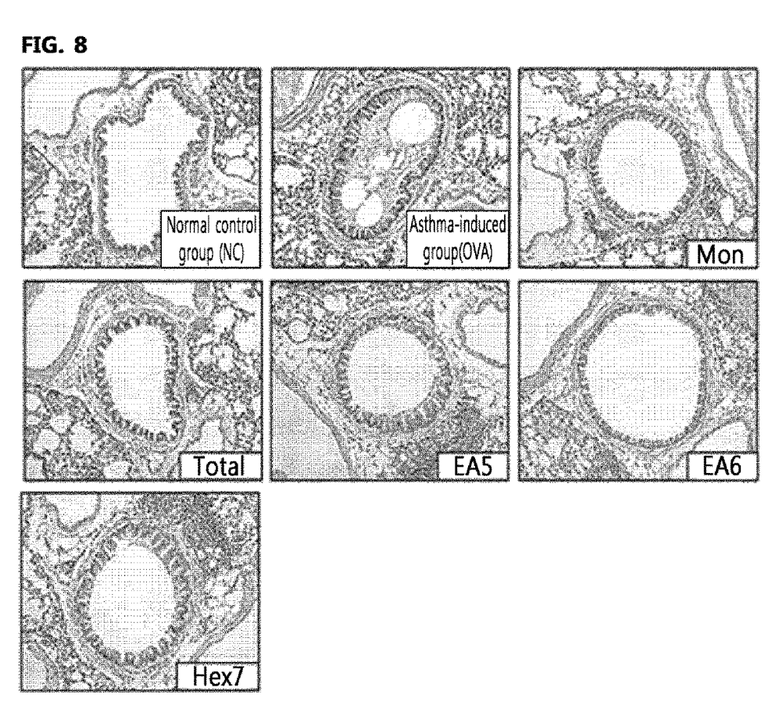
FIG. 8 shows the result of measuring effects of the total extract, hexane fraction and ethyl acetate fraction of *Pistacia weinmannifolia* on mucus secretion in the airway in ovalbumin-sensitized asthma animal models, NC: Normal control group whose airway was not sensitized OVA: Asthma-induced group whose airway was sensitized with ovalbumin Mon: Comparative group administered with montelukast Total: Experimental group administered with ethanol extract of *Pistacia weinmannifolia*

In a specific embodiment of the present invention, the methanol extract, the hexane fraction, and the ethyl acetate fraction of *Pistacia weinmannifolia* according to the present invention were also found to remarkably inhibit production of interleukin-4, 5, 13 in bronchoalveolar lavage fluid (see Table 2), infiltration of inflammatory cells to the airway (see FIG. 7), and mucus production in the airway (see FIG. 8).

These results suggest that the *Pistacia weinmannifolia* extract and the fractions thereof according to the present invention may be usefully applied to the prevention or treatment of asthma.

Accordingly, the present invention provides a composition for preventing or treating asthma, the composition including the *Pistacia weinmannifolia* extract or the fraction thereof as an active ingredient, and further including a pharmaceutically acceptable carrier.

Asthma is a kind of allergic diseases caused by allergic inflammation reactions of bronchial airways, generally resulting from hypersensitivity of the airways in the lung. Allergy is a phenomenon where a body develops a different response from a normal response when exposed to a foreign substance, and specifically, allergy involves recruitment and infiltration of a variety of inflammatory cells to the airways and tissues surrounding blood vessels, and various inflammatory mediators produced therefrom further increase inflammatory responses, resulting in an increase in mucus secretion and airway hyperresponsiveness.

As used herein, the term "prevention" means all of the actions by which the occurrence of asthma is restrained or retarded by administration of the composition according to the present invention.

As used herein, the term "treatment" means all of the actions by which the symptoms of asthma have taken a turn for the better or been modified favorably by administration of the composition according to the present invention.

The pharmaceutical composition of the present invention may be used singly or prepared as a formulation including a drug approved to have an anti-asthma effect as well as the extract or the fraction thereof.

The term "pharmaceutically acceptable" means that it does not cause significant irritation to an organism to which the compound is administered and does not abrogate the biological activity and properties of the compound.

The pharmaceutical composition including a pharmaceutically acceptable carrier of the present invention may be prepared into various formulations such as oral or parenteral formulations. The formulation of the composition may involve using general diluents or excipients such as fillers, bulking agents, binders, wetting agents, disintegrants, surfactants, etc. The solid formulations for oral administration may include tablets, pills, powders, granules, capsules, etc. The solid formulations may be prepared by mixing one or more compounds with at least one excipient, for example, starch, calcium carbonate, sucrose, lactose, gelatin, etc. In addition to such simple excipients, lubricants such as magnesium stearate or talc may also be used. The liquid formulation for oral administration may include suspensions, solutions for internal use, emulsions, syrups, etc. In addition to simple diluents commonly used, such as water and liquid paraffin, different excipients may also be used, for example, wetting agents, flavors, fragrances, preserves, etc. The formulations for parenteral administration may include sterile aqueous solutions, non-aqueous solvents, suspensions, emulsions, lyophilized preparations, and suppositories. The non-aqueous solutions and the suspensions may include propylene glycol, polyethylene glycol, vegetable oil such as olive oil, injectable ester such as ethyloleate, etc. The base for suppositories may include witepsol, macrogol, tween 61, cacao butter, laurin butter, glycerogelatin, etc.

The pharmaceutical composition may have any one formulation selected from the group consisting of tablets, pills, powders, granules, capsules, suspensions, solutions for internal use, emulsions, syrups, sterile aqueous solutions, non-aqueous solvents, suspensions, emulsions, lyophilized preparations, and suppositories.

The pharmaceutical composition of the present invention may include the *Pistacia weinmannifolia* extract or the fraction thereof in a pharmaceutically effective amount. As used herein, the term "pharmaceutically effective amount" refers to an amount sufficient to treat diseases, at a reasonable benefit/risk ratio applicable to any medical treatment. The effective dosage level may be determined depending on kind of the subject and severity, age, sex, activity of the drug, sensitivity to the drug, administration time, administration route and excretion rate, duration of treatment, drugs used simultaneously, and other factors known in the medical field. The pharmaceutical composition of the present invention may be administered alone or in combination with other therapeutic agents, and may be administered sequentially or simultaneously with existing therapeutic agents. The composition may be administered in a single or multiple dosage form. It is important to administer the composition in the minimum amount that can exhibit the maximum effect without causing side effects, considering all the above-described factors. Those skilled in the art may readily determine. The *Pistacia weinmannifolia* extract or the fraction thereof according to the present invention may be included in an amount of, specifically, 0.001 to 1500 µg/ml, and more specifically, 0.001 to 1000 µg/ml in the pharmaceutical composition.

In another aspect, the present invention provides a method of preventing or treating asthma, the method including administering the pharmaceutical composition including the *Pistacia weinmannifolia* extract or the fraction thereof according to the present invention to a subject in need of prevention or treatment of asthma.

The subject may be a subject in need of prevention or treatment of asthma or asthma-related diseases, and it may be, but is not limited to, a human and a mammal, such as cow, horse, sheep, pig, goat, camel, antelope, dog, cat, etc. as well as human in need of treatment of asthma or asthma-related diseases and symptoms similar thereto.

As used herein, the term "administration" means introduction of the pharmaceutical composition of the present invention into a patient by a certain suitable method. As long as it reaches target tissues, any route, whether oral or parenteral, may be taken for administering the composition of the present invention.

The method of treating asthma of the present invention may include administering the *Pistacia weinmannifolia* extract or the fraction thereof at a therapeutically effective amount. It is apparent to those skilled in the art that a total daily dose can be determined through appropriate medical judgment by a physician. Further, the composition may be administered once or several times. With respect to the objects of the present invention, the specific therapeutically effective dose level for any particular patient may vary depending on various factors well known in the medical art, including the kind and degree of the response to the achieved, concrete compositions according to whether other agents are used therewith or not, the patient's age, body weight, health conditions, sex, and diet, the time and route of administration, the secretion rate of the composition, the time period of therapy, other drugs used in combination or coincidentally with the specific composition, and like factors well known in the medical arts.

In still another aspect, the present invention provides a food composition for preventing or improving asthma, the food composition including the *Pistacia weinmannifolia* extract or the fraction thereof.

The *Pistacia weinmannifolia* extract or the fraction thereof is the same as described above.

The food composition may have a function of helping suppression of asthma occurrence.

The food composition of the present invention may include a type of pills, powders, granules, infusions, tablets, capsules, or liquid, and there is no limitation in the type of the food to which the *Pistacia weinmannifolia* extract of the present invention or the fraction thereof may be added. Example thereof may include a variety of drinks, gums, teas, vitamin complexes, health supplementary foods, etc.

The food composition may include an additional ingredient that does not disturb anti-asthma and anti-inflammatory activities, in addition to the *Pistacia weinmannifolia* extract or the fraction thereof, and there is no particular limitation in the type of the ingredient. For example, various herbal extracts, sitologically acceptable auxiliary food additives, natural carbohydrates, etc. may be further included as in common foods.

As used herein, the term "auxiliary food additive" refers to an ingredient that may be added supplementarily to foods, and is added to prepare each formulation of a health functional food. The auxiliary food additive may be adequately selected by those skilled in the art. Examples of the auxiliary food additive include various nutrients, vitamins, minerals (electrolytes), synthetic or natural flavors, colorants, fillers, pectic acid and salts thereof, alginic acid and salts thereof, organic acids, protective colloid thickeners, pH control agents, stabilizers, antiseptics, glycerin, alcohols, carbonating agents used in carbonated drinks, etc. However, the auxiliary food additive of the present invention is not limited to the above-described examples.

Examples of the natural carbohydrate include monosaccharides such as glucose, fructose, etc.; disaccharides such as maltose, sucrose, etc.; polysaccharides such as dextrin, cyclodextrin, etc.; and sugar alcohols such as xylitol, sorbitol, erythritol, etc. In addition, a natural sweetener (thaumatin, stevia extract (e.g., rebaudioside A, glycyrthizin, etc.)) or a synthetic sweetener (saccharin, aspartame, etc.) may be advantageously used as a sweetener.

The food composition of the present invention may be included in a health functional food. As used herein, the term "health functional food" refers to a food prepared or processed into tablet, capsule, powder, granule, liquid, pill, etc. using raw materials or ingredients with useful functions for the human body. Herein, the "functional" means a useful effect for human health, such as structural or functional regulation of nutrients, physiological action, or the like. The health functional food of the present invention may be prepared according to a method commonly employed in the art, and raw materials and ingredients commonly used in the art may be added when preparing the health functional food. Since food are used as raw materials, unlike general drugs, the health functional food lacks side effects which may occur when a drug is taken for a long period of time, and may have excellent portability.

The amount of the active ingredient to be mixed may be determined appropriately depending on the purpose of use (prevention, health improvement, or therapeutic intervention). In general, the *Pistacia weinmannifolia* extract or the fraction thereof according to the present invention may be added in an amount of 1~10% by weight, preferably, 5~10% by weight in the raw material composition, upon preparation of foods. However, the content may be lower then the above-described range when the health functional food is ingested for along period of time for promoting health and hygiene or for controlling health.

The kind of food is not particularly limited. Examples of the food to which the material may be added include meat, sausage, bread, chocolate, candy, snack, confectionery, pizza, ramen, other noodles, gum, dairy products including ice cream, soup, beverage, tea, drink, alcoholic beverages, vitamin complex, etc. All health functional foods in the context of common sense are included.

In still another aspect, the present invention provides use of the *Pistacia weinmannifolia* extract or the fraction thereof in the preparation of a medicament for preventing or treating asthma. The medicament may be administered orally or parenterally to a subject for the prevention or treatment of asthma, and may be provided in the form of proper formulations according to characteristics of the subject. Further, the medicament may be prepared by including the extract or fraction in a proper amount, if necessary.

In still another aspect, the present invention provides a method of treating asthma, the method including administering the pharmaceutical composition to a subject suspected of having asthma.

In an embodiment of the present invention, administration of the *Pistacia weinmannifolia* extract to an animal model was found to effectively inhibit secretion of immunoglobulins in the serum, mucus secretion in the airway, and infiltration of inflammatory cells to the lung tissue (FIGS. 4 to 8), thereby providing a method of effectively treating asthma by administering the *Pistacia weinmannifolia* extract or the fraction thereof to a subject.

Hereinafter, the constitution and effect of the present invention will be described in more detail with reference to Examples. However, these Examples are for illustrative purposes only, and the scope of the present invention is not intended to be limited by these Examples.

PREPARATION EXAMPLE 1

Preparation of *Pistacia Weinmannifolia* Stem Extract

*Pistacia weinmannifolia* (*Pistacia weinmannifolia* J. Poiss, Ex Franch) was collected inn Yunnan province (Shilin county, Shilin town, Sanjia village) of China and identified in 2013 (Korea Research Institute Of Bioscience And Biotechnology, Dr. Sang Woo Lee), and an ethanol extract thereof was prepared in YAAS (Yunnan academy of agricultural sciences) and delivered to International Biological Material Research Center, Korea Research Institute Of Bioscience And Biotechnology. The present inventors obtained samples from a plant extract bank at the center and performed the following experiment.

According to the extraction process, 10 kg of the stem of *Pistacia weinmannifolia* was collected, and naturally dried (shade drying) to remove water, followed by pulverization. Each 5 kg of the powder sample thus pulverized was put in a container, and 10 L of ethanol (95%) was added thereto, followed by precipitation extraction under intermittent stirring at room temperature (20° C.) for 10 days. Thereafter, the extract was filtered through a filter paper, and the remaining solvent and water were concentrated under reduced pressure by heating in warm water of 40° C. or lower to obtain 542.2 g of an ethanol extract of *Pistacia weinmannifolia*. In a subsequent experiment, the obtained ethanol extract of *Pistacia weinmannifolia* was called Total extract.

PREPARATION EXAMPLE 2

Preparation of *Pistacia Weinmannifolia* Fractions

5 L of water was added to 542.2 g of Total extract of *Pistacia weinmannifolia* obtained in Preparation Example 1 and then suspended. An equal amount of hexane was added to separate an aqueous layer and a hexane layer. This procedure was further repeated three times in the same manner, and filtration and concentration under reduced pressure were performed to separate a hexane fraction (48.5 g). To the aqueous layer remaining after separating the hexane layer in the same manner, an equal amount of chloroform was added and separation was performed in the same manner as above to obtain a chloroform fraction (16.3 g). To the aqueous layer remaining after separating the chloroform layer in the same manner, an equal amount of ethyl acetate was added and separation was performed in the same manner as above to obtain an ethyl acetate fraction (53.7 g). To the aqueous layer remaining after separating the ethyl acetate layer in the same manner, an equal amount of butanol was added and separation was performed in the same manner as above to obtain a butanol fraction (114 g). The remaining aqueous layer was concentrated to obtain a water fraction (186.5 g).

PREPARATION EXAMPLE 3

Analysis of Active Fractions of *Pistacia Weinmannifolia* Fractions

In order to examine active fractions of the hexane fraction and ethyl acetate fraction of *Pistacia weinmannifolia*, which were obtained in <Preparation Example 2>, these fractions were analyzed by two types of liquid chromatography, UPLC (ultra performance liquid chromatography) and MPLC (Medium pressure liquid chromatography).

First, for UPLC analysis, the hexane fraction (48.5 g) and the ethyl acetate fraction (53.7 g) were filtered using a 0.25 mm membrane filter for UPLC once. A column (Waters BEH C18 column, 2.1×100 mm, 1.7 mm) was placed in a UPLC instrument (Waters UPLC-Q-TOF), and then each of the filtered fractions was loaded in an amount of 0.3 μl. In this regard, acetonitrile+0.1% formic acid/water+0.1% formic acid [10:60→100:0 (v/v)] were used as a solvent, and an elution rate was 0.4 ml/min and detection was performed at a wavelength of UV 200-400 nm.

Figure 1:
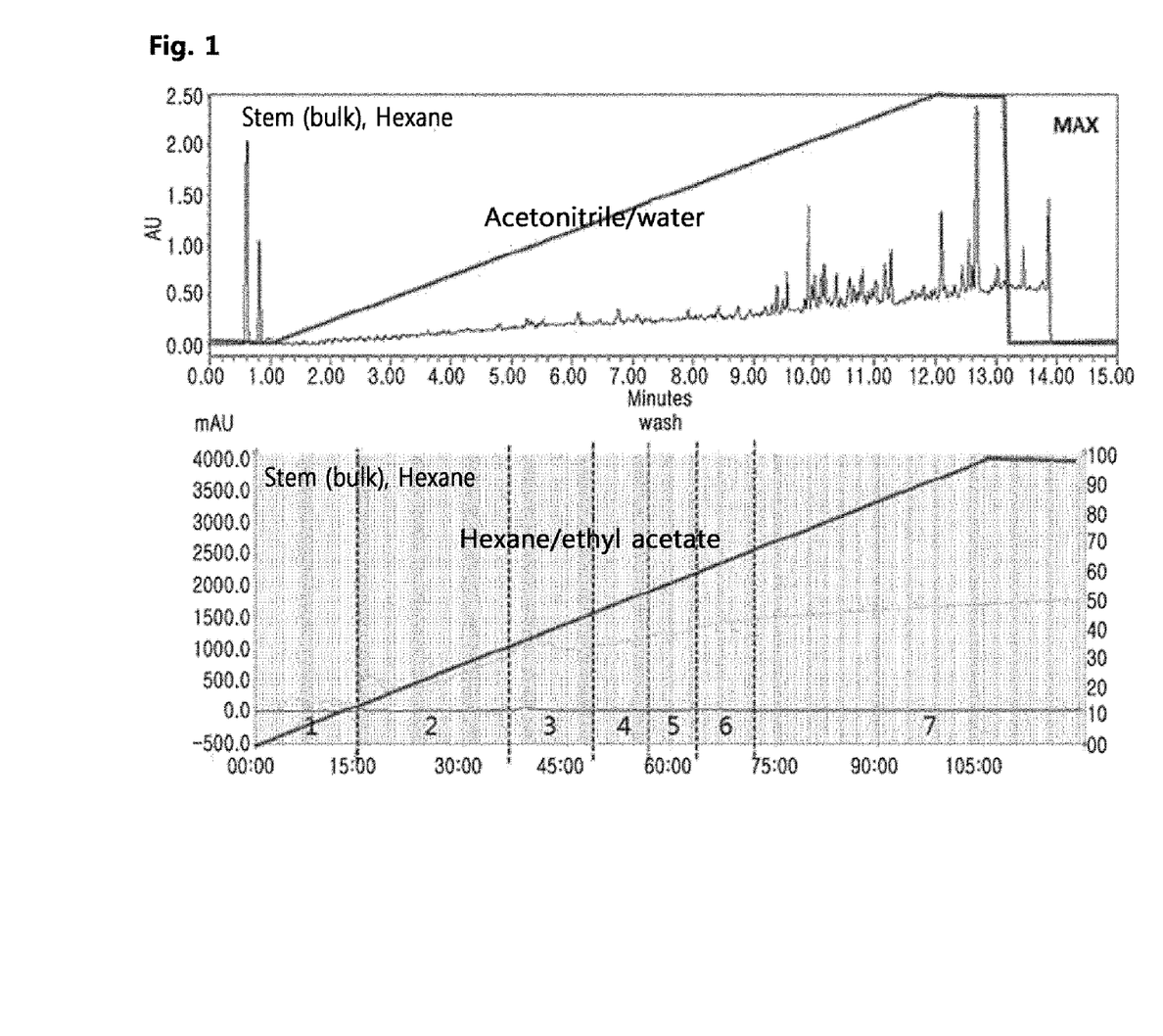
FIG. 1 shows the result of UPLC (Ultraperformance Liquid Chromatography) analysis of a hexane fraction of *Pistacia weinmannifolia*.
Figure 2:
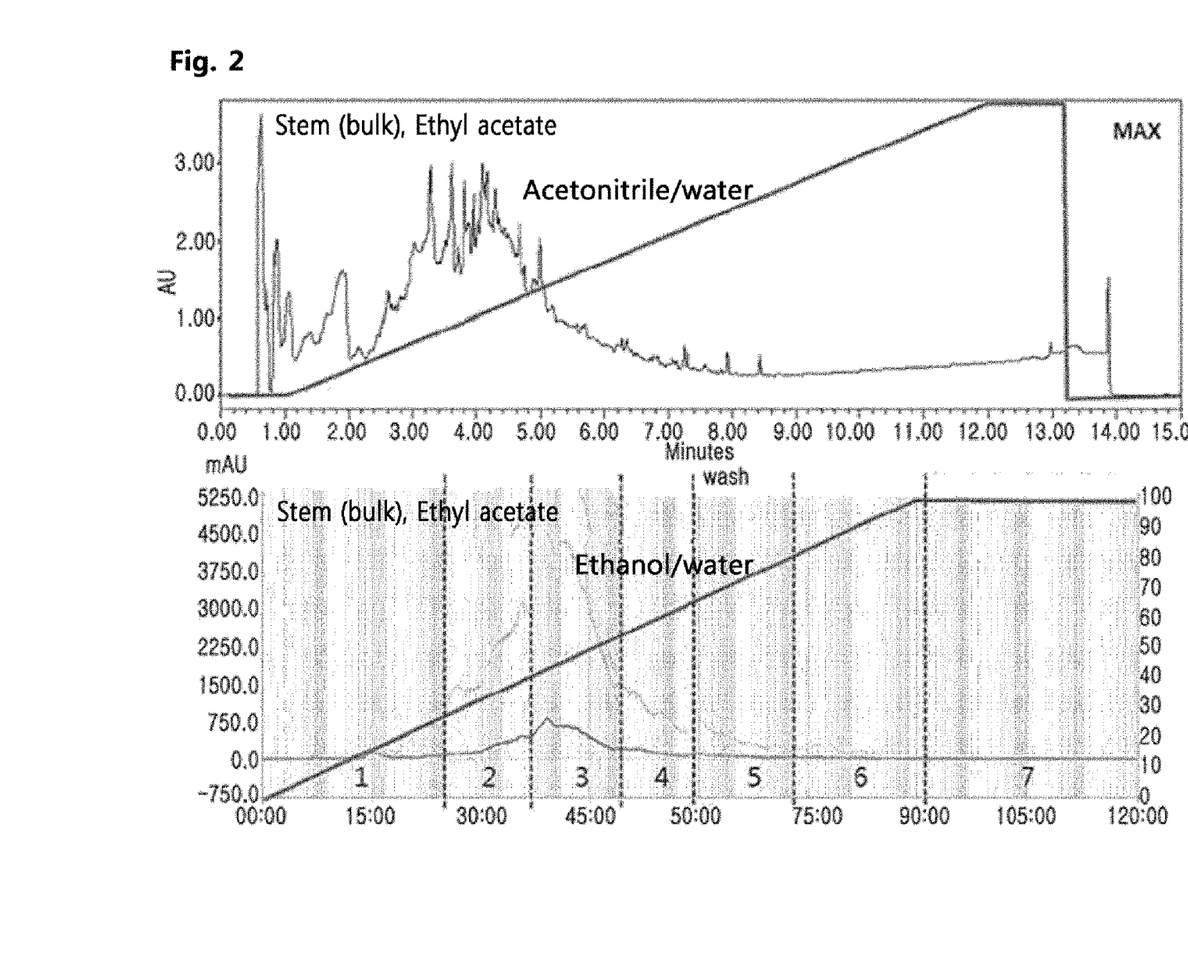
FIG. 2 shows the result of UPLC analysis of an ethyl acetate (EtOAc) fraction of *Pistacia weinmannifolia*.

For MPLC analysis, a column (20 mm×250 mm; Resin: Zeoprep C18, 10 m) was placed in a MPLC instrument (Interchim), and then each 1 g of the hexane and ethyl acetate fractions was loaded. In this regard, hexane/ethyl acetate [0:90-100:0 (v/v)] was used as a solvent, and an elution rate was 9 ml/min and detection was performed at a wavelength of UV 200-400 nm. Analysis was performed for 110 minutes for the hexane fraction and for 120 minutes for the ethyl acetate fraction The results of UPLC and MPLC analysis are shown in FIGS. 1 and 2, and the result of UPLC analysis is shown in the upper panel of each figure and the result of MPLC analysis is shown in the lower panel of each figure.

EXAMPLE 1

Evaluation of Anti-inflammatory Effect in LPS-induced Macrophage

<1-1> Inhibitory effect on nitric oxide (NO) production

In order to examine anti-inflammatory effects of the *Pistacia weinmannifolia* extract and the fractions thereof, lipopolysaccharide (LPS)-stimulated nitric oxide (NO) production in mouse macrophage cells, RAW 264.7 was measured.

In detail, cells were inoculated and suspended at a density of $2.5 \times 10^5$ cells/ml in phenol red-free DMEM (Dulbecco's Modified Eagle Medium, Gibco) supplemented with 5% fetal bovine serum, and 200 µl thereof was inoculated in a 96-well plate. After induction of cell adhesion for 4 hours, the cells were treated with each 20 µg/ml of the samples, and then incubated for 1 hour. Subsequently, the cells were treated with 0.5 µg/ml of LPS, and further cultured for 24 hours. Thereafter, 100 µl of the supernatant was collected and aliquoted in a new 96-well plate, and an equal amount of Griess reagent (Sigma) was added thereto and allowed to react at room temperature for 10 minutes. Then, absorbance at 540 nm was measured using a microplate reader (Bio-Rad). A standard curve was plotted using sodium nitrite, and on the basis of this curve, a production amount of nitric oxide in the culture was calculated. The NO production amount of LPS-treated group was regarded as 100% to calculate an inhibition rate of each sample. In this regard, the samples were the ethanol extract (Total), hexane fraction (Hexane), chloroform fraction (CHCl3), ethyl acetate fraction (EA), butanol fraction (BuOH), and water fraction (Aq) obtained in Preparation Examples 1 and 2.

Figure 3A:
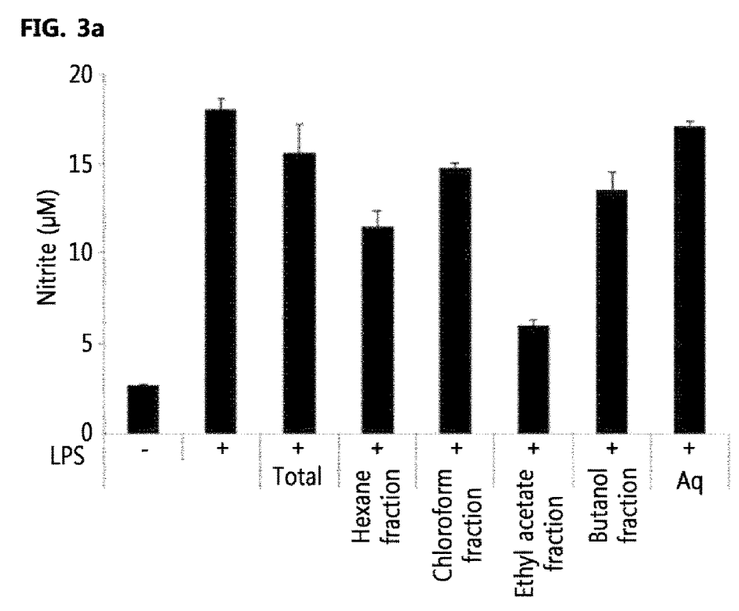
FIG. 3a shows the result of measuring effects of an ethanol extract (Total), a hexane fraction (Hexane), chloroform fraction ($CHCl_3$), an ethyl acetate fraction (EA), a butanol fraction (BuOH), and a water fraction (Aq) of *Pistacia weinmannifolia* on LPS-induced nitric oxide (NO) production in macrophages.

As shown in FIG. 3a, NO production was rapidly increased in the cells treated with only LPS, whereas NO production was decreased in the cells which were pre-treated with the ethanol extract or various fractions and then treated with LPS. In particular, when cells were pre-treated with the hexane fraction (36.24±5.01% inhibition) or the ethyl acetate fraction (66.71±1.71% inhibition), NO production was remarkably decreased.

Figure 3B:
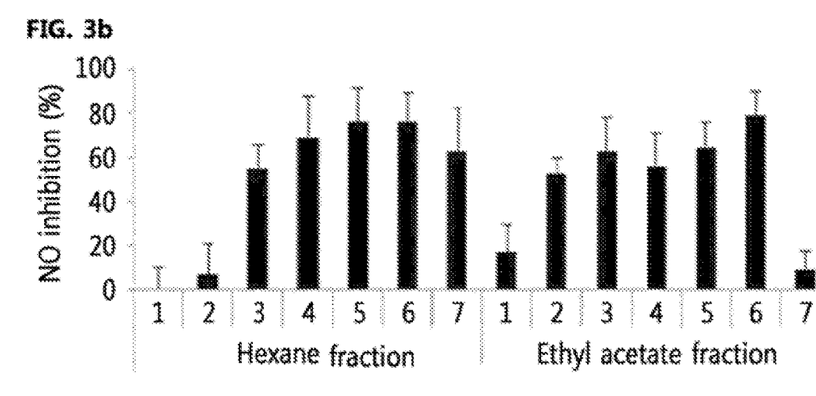
FIG. 3b shows the result of measuring effects of Active fraction 1 to 7(Hex 1-7) of the hexane fraction and Active fraction 1 to 7(EA 1-7) of the ethyl acetate fraction of *Pistacia weinmannifolia* on LPS-induced nitric oxide (NO) production in macrophages.

As shown in FIG. 3b, among the active fractions of the hexane fraction and the ethyl acetate fraction examined in Preparation Example 3, Active fraction 3 to 7 of the hexane fraction and Active fraction 2 to 6 of the ethyl acetate fraction were found to decrease NO production.

<1-2> Effect on cell viability

In order to examine the effect of the *Pistacia weinmannifolia* extract and the fraction on cell viability, as in Example <1-1>, Raw 264.7 cells were inoculated and suspended at a density of $1 \times 10^5$ cells/ml in DMEM (Dulbecco's Modified Eagle Medium, Gibco) supplemented with 5% fetal bovine serum, and 100 µl thereof was inoculated in a 96-well plate. After induction of cell adhesion for 4 hours, the cells were treated with each 20 µg/ml of the samples, and then cultured for 24 hours. Subsequently, 10 µl of 5 mg/ml MTT solution was added to each well, and further cultured for 4 hours. Thereafter, the supernatant was discarded and 100 µl of DMSO was added. Then, absorbance at 570 nm was measured. Cell viability was calculated by the following Equation 1, when the value of 0.2% DMSO-treated negative control group was regarded as 100%.

$$\text{Cell visibility (\%)} = [\text{OD}_{570nm} \text{ value of extract-treated group}/\text{OD}_{570nm} \text{ value of negative control group}] \times 100 \quad \text{[Equation 1]}$$

Figure 3C:
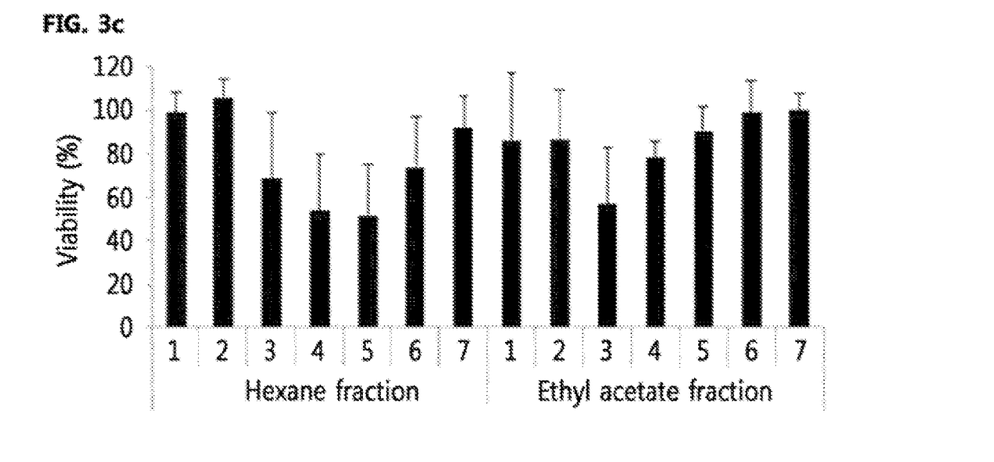
FIG. 3c shows the result of measuring effects of Active fraction 1 to 7(Hex 1-7) of the hexane fraction and Active fraction 1 to 7(EA 1-7) of the ethyl acetate fraction of *Pistacia weinmannifolia* on cell viability of macrophages.

As shown in FIG. 3c, active fractions showing cell viability of 80% or more were Active fraction 1, 2, and 7 of the hexane fraction and Active fraction 1, 2, and 5 to 7 of the ethyl acetate fraction.

Accordingly, the present inventors selected Active fraction 7 (62.84±19.61% inhibition) of the hexane fraction and Active fraction 5 and 6 (each 64.42±11.2% and 78.88±11.20% inhibition) of the ethyl acetate fraction which show excellent inhibitory effect on NO production and high cell viability due to low toxicity, and they used the fractions in the subsequent experiments.

EXAMPLE 2

Evaluation of Asthma Relief Effect in Ovalbumin-sensitized Asthma Animal Model

<2-1> Experimental animals and induction of bronchial asthma

In the present experiment, 6-week-old Balb/c female mice having a body weight of about 20 g in average were used as experimental animals. After 1 week of acclimation, animals showing no abnormal findings on physical examination were used as subjects. 2 mg of aluminium hydroxide (A8222, Sigma, St. Louis, Mo.) and 20 µg of ovalbumin (A5503, Sigma, St. Louis, Mo.) were suspended in 200 µl of phosphate buffer (pH 7.4) and then injected into the peritoneal cavity of mouse for sensitization. On days 21 to 23 after the first intraperitoneal administration of ovalbumin, inhalation challenge was performed for 30 min with 1% ovalbumin using an ultrasonic atomizer. 24 hours after the last antigen administration, airway hyperresponsiveness was measured. 48 hours later, a lethal dose of pentobarbital (Entobal, Hanlim Pharmaceutical Co., Ltd.) was administered, body weight measurement and bronchotomy were performed, and bronchoalveolar lavage was performed with a total 1.2 mL of physiological saline, and then, samples were collected. Experiments were proceeded with a normal control group (NC) in which mice were not administered with ovalbumin and not challenged with ovalbumin inhalation, an asthma-induced group (OVA) in which mice were administered with ovalbumin and challenged with ovalbumin inhalation, and bronchial asthma was induced, a comparative group (Mon) in which mice were orally administered with montelukast (30 mg/kg, PO) 1 hour prior to ovalbumin inhalation, an experimental group in which mice were orally administered with the ethanol extract (30 mg/kg, PO; Total), Active fraction 5 of the ethyl acetate fraction (30 mg/kg, PO; EA5), Active fraction 6 of the ethyl acetate fraction (30 mg/kg, PO; EA6), and Active fraction 7 of the hexane fraction (30 mg/kg, PO; Hex7), respectively 1 hour prior to ovalbumin inhalation. Seven white mice were used for each group.

<2-2> Measurement of airway hyperresponsiveness

Airway hyperresponsiveness caused by asthma occurrence was examine by measuring airway resistance with one chamber plethysmography (All medicus, Seol) and the degree of airway resistance was evaluated by measuring enhanced pause (Penh) that indicated mathematically calculated airway obstruction. To measure Penh, the baseline value was measured under a normal respiratory condition, and then PBS was inhaled using an ultrasonic atomizer for 3 minutes, and Penh values were measured over 3 minutes. then, gradually increasing concentrations (12, 25 and 50 mg/ml) of methacholine (A2251, Sigma, St. Louis, Mo.) was inhaled, followed by measurement of Penh. Penh value was calculated according to the following Equation 2, and an increase rate in Penh after inhalation of each concentration of methacholine was expressed as a percentage, when the baseline Penh (PBS challenge) was regarded as 100%.

$$Penh = \left[\frac{Te}{RT-1}\right] \times \left(\frac{PEF}{PIF}\right) \quad \text{[Equation 2]}$$

Figure 4:
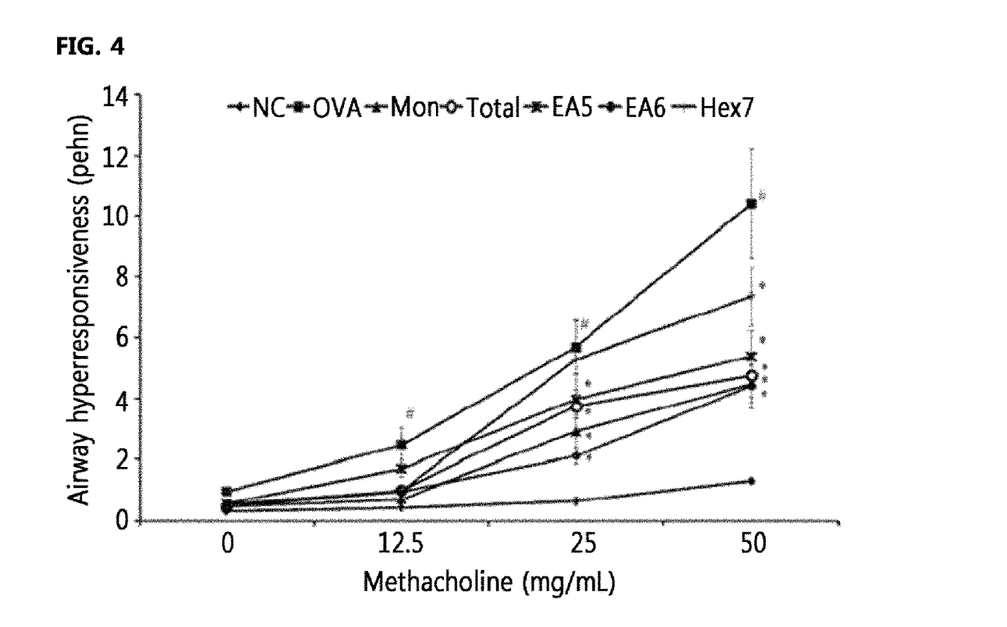
FIG. 4 shows the result of measuring effects of the total extract, hexane fraction and ethyl acetate fraction of *Pistacia weinmannifolia* on airway hyperresponsiveness in ovalbumin-sensitized asthma animal models, NC: Normal control group whose airway was not sensitized OVA: Asthma-induced group whose airway was sensitized with ovalbumin Mon: Comparative group administered with montelukast Total: Experimental group administered with Total extract of *Pistacia weinmannifolia*

Te: expiratory time (sec) (the time from inspiration to the next inspiration)
RT: relaxation time (the elapsed time between the beginning of the expiration and the moment when the remaining 30% of the tidal volume has been reached during expiration)
PEF: Peak expiration flow
PIF: Peak inspiration flow As a result, as shown in FIG. 4, the normal control (NC) group showed a slow increase in Penh value as the concentration of methacholine increased, but the asthma-induced group (OVA) showed an abrupt increase in Penh value. However, the Penh value in the comparative group (M) administered with montelukast and the experimental groups (Total, EA5, EA6, Hex7) administered with the *Pistacia weinmannifolia* extract and the fraction thereof significantly decreased, compared to that in the asthma-induced group (OVA), in a manner dependent on the concentration.

EXAMPLE 3

Measurement of Serum Ige and Ovalbumin-specific Ige Antibody

To measure serum IgE and ovalbumin-specific IgE, an immunoenzymatic assay was used. IgE level was measured using a commercially available kit (Biolegend Ins., California, USA). To measure ovalbumin-specific IgE level, 20 μg/mL of ovalbumin was dissolved in a 0.1 M NAHCO$_3$ buffer (pH 8.3), and was placed into a 96-well flat bottom ELISA plate to be coated at 4° C. overnight. Nonspecific binding was blocked with PBS containing 1% bovine serum albumin. A serum sample was diluted 1:400 and added to the well plate and was allowed to react at room temperature for 2 hours. Then, the plate was washed well, and anti-mouse IgE monoclonal antibody (Biolegend Ins., California, USA) was diluted 1:300 and was allowed to react for 2 hours. Then, HRP-conjugated goat anti-mouse IgG polyclonal antibody (Biolegend Ins., California, USA) which was coupled to peroxidase was diluted 1:4000, added to the well plate, and allowed to react at room temperature for 1 hour, and then washed. For color development, 3,3',5,5'-tetramethyl-bezidine substrate was allowed to react, and the spectroscopic absorbance was measured at 450 nm. In this regard, for statistical analyses, mean values and standard errors (mean±S.E.) according to a number of variables were calculated, and comparison between each group was analyzed by performing a Mann-whitney U test using SPSS 10.0. $p<0.05$ was considered statistically significantly different.

As shown in the following Table 1, serum IgE antibody level was greatly increased in the asthma-induced group (OVA) (2.4±0.34 μg/ml), compared to the normal control group (NC) (0.2±0.16 μg/ml), and significantly reduced in the montelukast administration group (Mon) (1.8±0.28 μg/ml), compared to the asthma-induced group (OVA). When the *Pistacia weinmannifolia* extract or the fraction thereof of the present invention was treated, the serum IgE antibody level was remarkably reduced, compared to the asthma-induced group (OVA), measured as 1.8±0.19 μg/ml in the Total administration group, 1.68±0.43 μg/ml in the EA5administration group, 1.5±0.24 μg/ml in the EA6administration group, and 2.0±0.41 μg/ml in the Hex7administration group. In particular, the reduction was prominent in the EA6administration group. The ovalbumin-specific IgE antibody level was also reduced, compared to the asthma-induced group (OVA) (368±90.6 ng/ml), as low as 2.37±41.9 ng/ml in the Total administration group, 169±55.8 ng/ml in the EA5administration group, 195±67.6 ng/ml in the EA6administration group, and 196±52 ng/ml in the Hex7administration group. Consequently, it was confirmed that ovalbumin-specific IgE antibody level is significantly reduced in the group treated with the *Pistacia weinmannifolia* extract or the fraction thereof of the present invention, compared to the asthma-induced group (OVA).

TABLE 1

| Group | IgE (ng/ml) | OVA-specific IgE (ng/ml) |
|---|---|---|
| NC | 0.2 ± 0.16 | — |
| OVA | 2.4 ± 0.34[#] | 368 ± 90.6[#] |
| Non | 1.8 ± 0.28* | 108 ± 83.0* |
| Total | 1.8 ± 0.19* | 237 ± 41.9* |
| EA5 | 1.7 ± 0.43* | 169 ± 55.8* |
| EA6 | 1.5 ± 0.24* | 105 ± 67.6* |
| Hex7 | 2.0 ± 0.41 | 196 ± 52.1* |

[#]considered statistically significant, compared to normal control group (NC) (p < 0.05),
*considered statistically significant, compared to asthma-induced group (OVA) (p < 0.05).

EXAMPLE 4

Analysis of Inflammatory Cells in Bronchoalveolar Lavage Fluid

Bronchoalveolar lavage fluid was collected from individuals, and immediately after the collection, fluid was stained with trypan blue. The number of total cells except dead cells was calculated using a hemocytometer. Subsequently, Diff-Quick staining (Sysmex, Swizerland) was performed after smear preparation with Cytospin II, and eosinophils and other inflammatory cells were differentially counted.

As shown in FIG. 5, the number of eosinophils was greatly increased in the asthma-induced group (OVA) measured as $(74\pm16.0)\times10^5$, compared to the normal control group (NC) (0±0), whereas it was reduced in the montelukast administration group (Mon), measured as $(36\pm20.4)\times10^5$. When the *Pistacia weinmannifolia* extract or the fraction thereof of the present invention was treated, the number of eosinophils was remarkably reduced, compared to the asthma-induced group (OVA), measured as $(32\pm4.1)\times10^5$ in the Total administration group, $(42\pm6.1)\times10^5$ in the EA5administration group, $(23\pm7.4)\times10^5$ in EA6administration group, and $(41\pm10.7)\times10^5$ in the Hex7administration group. These reductions were similar to or more significant than that of the montelukast administration group (Mon) as the comparative group. In particular, the reduction was prominent in the EA6administration group.

The number of total inflammatory cells including other inflammatory cells was greatly increased in the asthma-induced group (OVA) measured as $(180\pm22.2)\times10^5$, compared to the normal control group (NC) measured as $(9\pm2.0)\times10^5$, whereas it was significantly reduced in the montelukast administration group (Mon), measured as $(98\pm19.3)\times10^5$, compared to the asthma-induced group (OVA). When the *Pistacia weinmannifolia* extract or the fraction thereof of the present invention was treated, the number of total inflammatory cells was remarkably reduced, compared to the asthma-induced group (OVA), measured as $(126\pm16.3)\times10^5$ in the Total administration group, $(140\pm20.3)\times10^5$ in the EA5administration group, $(83\pm17.7)\times10^5$ in the EA6administration group, and $(133\pm11.6)\times10^5$ in the Hex7administration group. In particular, the reduction was prominent in the EA6administration group.

EXAMPLE 5

Inhibitory Effect on Reactive Oxygen Species Generation

A portion of the bronchoalveolar lavage fluid of each individual was washed with phosphate buffer solution (PBS), and 10 mM 2,7-dichlorofluorescein diacetate (35845, Sigma, St. Louis, Mo.) was added thereto. The bronchoalveolar lavage fluid was left at from temperature in a dark room for 10 minutes, and a hemocytometer was used for measurement (Ex=480 nm, Em=522 nm).

Consequently, as shown in FIG. 6, the generation amount of reactive oxygen species was greatly increased in the asthma-induced group (OVA), compared to the normal control group (NC). In contrast, when the *Pistacia weinmannifolia* extract or the fraction thereof of the present invention was treated, the generation amount of reactive oxygen species was reduced, compared to the asthma-induced group (OVA), measured as 42.7% in the Total administration group, 25.4% in the EA5administration group, 46.3% in the EA6administration group, and 36.1% in the Hex7administration group.

EXAMPLE 6

Inhibitory Effect on Production of Interleukin-4, 5, and 13 in Bronchoalveolar Lavage Fluid In order to measure effect of the *Pistacia weinmannifolia* extract of the fraction thereof of the present invention on the production of interleukin-4, 5, and 13 in bronchoalveolar lavage fluid, a commercially available ELISA kit (R&D Systems, Inc., Minneapolis, Minn., USA) was used.

Briefly, 100 μl of bronchoalveolar lavage fluid was added to a well plate and allowed to react for 1 hour. After reaction, the plate was washed using a washing solution in the ELISA kit, and 100 μl of conjugate suitable for each kit was added and allowed to react for 2 hours. After completion of the reaction, the well plate was washed using a washing solution. For color development, 100 μl of a substrate solution in each kit was added and allowed to react for 30 minutes, and 100 μl of a stop solution in the kit was added to terminate the reaction. Absorbance was measured at 450 nm. In this regard, for statistical analyses, mean values and standard errors (mean±S.E.) according to a number of variables were calculated, and comparison between each group was analyzed by performing a Mann-whitney U test using SPSS 10.0. $p<0.05$ was considered statistically significantly different.

Consequently, as shown in the following Table 2, the production amount of interleukin-4 in bronchoalveolar lavage fluid was greatly increased in the asthma-induced group (OVA) measured as 67.6±11.51 pg/ml, compared to the normal control group (NC) (27.7±5.68 pg/ml). In contrast, when the *Pistacia weinmannifolia* extract or the fraction thereof of the present invention was treated, the production amount of interleukin-4 was reduced, compared to the asthma-induced group (OVA), measured as 44.5±6.93 pg/ml in the Total administration group, 43.6±6.93 pg/ml in the EA5administration group, 43.5±12.84 pg/ml in the EA6administration group, and 64.6±6.34 pg/ml in the Hex7administration group. The production amounts of interleukin-5 and 13 were also remarkably inhibited in the Total administration group, the EA5administration group, the EA6administration group, and the Hex7administration group, compared to the asthma-induced group (OVA).

TABLE 2

| Group | IL-4 (pg/ml) | IL-5 (pg/ml) | IL-13 (pg/ml) |
| --- | --- | --- | --- |
| NC | 27.7 ± 6.68 | 25.4 ± 3.62 | 19.6 ± 1.29 |
| OVA | 67.6 ± 11.51# | 67.3 ± 13.39# | 135.2 ± 25.33# |
| Non | 34.6 ± 6.52* | 32.4 ± 4.46* | 65.7 ± 18.86* |
| Total | 44.5 ± 6.93* | 42.4 ± 6.58* | 75.6 ± 9.48* |
| EA5 | 43.6 ± 8.00* | 44.0 ± 8.11* | 84.6 ± 10.29* |
| EA6 | 43.5 ± 12.84* | 39.0 ± 8.85* | 68.4 ± 15.00* |
| Hex7 | 64.6 ± 6.34 | 53.4 ± 9.10* | 101.81 ± 23.81* | considered statistically significant, compared to normal control group (NC) ($p < 0.05$),
*considered statistically significant, compared to asthma-induced group (OVA) ($p < 0.05$).

EXAMPLE 7

Histopathological Analysis of Asthma Animal Model

In order to evaluate the effect of the *Pistacia weinmannifolia* extract or the fraction thereof of the present invention on inflammation in the lung tissue, extracted lung tissue was generally fixed with formalin, embedded in paraffin and sectioned to a thickness of 4 μm. The tissue section was stained with H&E (Hematoxyin & Eosin) to evaluate inflammation in the lung tissue.

In order to evaluate the effect of the *Pistacia weinmannifolia* extract or the fraction thereof of the present invention on mucus secretion in the airway, periodic acid schiff staining (IMEB Inc., San Marcos, Calif.) was performed.

Consequently, as shown in FIG. 7, marked infiltration of inflammatory cells to the airways and tissues surrounding blood vessels was observed in the asthma-induced group (OVA), compared to the normal control group (NC). In contrast, when the *Pistacia weinmannifolia* extract or the fraction thereof of the present invention was treated, infiltration of inflammatory cells to the airways and tissues surrounding blood vessels was remarkably reduced in the Total administration group, and the EA5administration group, the EA6administration group, and the Hex7administration group, compared to the asthma-induced group (OVA).

As shown in FIG. 8, mucus secretion in the airway was remarkably increased in the asthma-induced group (OVA), compared to the normal control group (NC). In contrast, when the *Pistacia weinmannifolia* extract or the fraction thereof of the present invention was treated, mucus secretion in the airway was greatly reduced in the Total administration group, the EA5administration group, the EA6administration group, and the Hex7administration group, compared to the asthma-induced group (OVA).

EXAMPLE 8

Measurement of Cytotoxicity Of *Pistacia Weinmannifolia* Extract and Fraction Thereof In order to examine cytotoxicity of the *Pistacia weinmannifolia* extract and the fractions thereof prepared in Preparation Examples 1 and 2, BALB/c mouse-derived RAW 264.7 macrophages were used to perform the following experiment.

First, RAW 264.7 macrophages were suspended in DMEM supplemented with 10% fetal bovine serum (FBS), penicillin (100 U/ml) and streptomycin (100 µg/ml), and the cells were seeded into each well of a 96-well plate at a density of $5 \times 10^4$ cells, followed by culture at 5% $CO_2$ and 37° C. for 4 hours. After the cells were stabilized, the medium was replaced by a medium containing the ethanol extract of *Pistacia weinmannifolia*, the hexane fraction of *Pistacia weinmannifolia* or ethyl acetate fraction of *Pistacia weinmannifolia* obtained in Preparation Examples at a concentration of 5, 10, 20, or 40 µg/ml, followed by culture at 5% $CO_2$ and 37° C. for 18 hours. After completion of the culture, WST-1 reagent was added, followed by culture under conditions of 5% $CO_2$ and 37° C. for 3 hours. Absorbance at 450 nm was measured.

As a result, it was confirmed that the *Pistacia weinmannifolia* extract and the fractions thereof of the present invention generally showed no cytotoxicity at a concentration inducing the prophylactic or therapeutic effect on asthma, and therefore, they way be safely used in drugs for prevention, improvement or treatment of asthma, health functional foods, functional feeds, etc.

Taken together, it was confirmed that the *Pistacia weinmannifolia* extract of the present invention and the fractions thereof have high anti-asthma and anti-inflammatory activities.

Hereinbelow, Formulation Examples for the composition of the present invention will be described.

FORMULATION EXAMPLE 1

Preparation of Pharmaceutical Formulations

Pharmaceutical formulations including the *Pistacia weinmannifolia* extract of the present invention or the fraction thereof were prepared according to a general method as follows.
1. Preparation of powder
2. of *Pistacia weinmannifolia* extract or fraction thereof prepared in Preparation Example 1 or 2
1 g of lactose
The above ingredients were mixed, and filled into an airtight bag to prepare a powder.

2. Preparation of tablet
100 mg of *Pistacia weinmannifolia* extract or fraction thereof prepared in Preparation Example 1 or 2
100 mg of corn starch
100 mg of lactose
2 mg of magnesium stearate
The above ingredients were mixed, and tabletted according to a general tablet preparation method to prepare a tablet.
3. Preparation of capsule
100 mg of *Pistacia weinmannifolia* extract or fraction thereof prepared in Preparation Example 1 or 2
100 mg of corn starch
100 mg of lactose
2 mg of magnesium stearate
The above ingredients were mixed, and filled in a gelatin capsule according to a general capsule preparation method to prepare a capsule.
4. Preparation of pill
1 g of *Pistacia weinmannifolia* extract or fraction thereof prepared in Preparation Example 1 or 2
1.5 g of lactose
1 g of glycerin
0.5 g of xylitol
The above ingredients were mixed to prepare a pill (4 g per pill) according to a general preparation method.
5. Preparation of granule
150 mg of *Pistacia weinmannifolia* extract or fraction thereof prepared in Preparation Example 1 or 2
50 mg of soybean extracts
200 mg of glucose
600 mg of starch
The above ingredients were mixed, 100 mg of 30% ethanol was added thereto, and the mixture was dried at 60° C. to form granules, and then filled into a bag.

FORMULATION EXAMPLE 2

Preparation of Health Functional Food

Health functional foods including the *Pistacia weinmannifolia* extract of the present invention or the fraction thereof were prepared according to a general method as follows.
1. Preparation of wheat flour foods
0.5-5.0 parts by weight of the *Pistacia weinmannifolia* extract or fraction thereof prepared in Preparation Example 1 or 2 of the present invention were added to wheat flour, and bread, cakes, cookies, crackers, and noodles were prepared using the mixture.
2. Preparation of dairy products
Various dairy products such as butter and ice cream were prepared by adding 5~10% by weight of the Pistacia weinmannifolia extract or fraction thereof prepared in Preparation Example 1 or 2 of the present invention to milk and using the mixture.
3. Preparation of Sunsik (Grain Powder)
Brown rice, barley, glutinous rice and adlay were gelatinized by a general method, followed by drying. the dried mixture was distributed and pulverized, resulting in 60-mesh size grain powders. Black bean, black sesame and perilla were steamed and dried by a general method. The dried mixture was distributed and pulverized, resulting in 60-mesh size grain powders. The *Pistacia weinmannifolia* extract or fraction thereof prepared in Preparation Example 1 or 2 of the present invention was concentrated under reduced pressure using a vacuum concentrator, which was then spray-dried with a hot-air drier. The dried material was pulverized by a grinder, resulting in 60-mesh size grain powders.

The grains, seeds, and dry powder of Pistacia weinmannifolia extract or fraction were mixed at the following ratio.

Grains (30% by weight of brown rice, 15% by weight of adlay, 20% by weight of barley), Seeds (7% by weight of perilla, 8% by weight of black bean, 7% by weight of black sesame), Dry powder of *Pistacia weinmannifolia* extract or fraction (3% by weight), Granoderma lucidum (0.5% by weight), Rehmannia glutinosa (0.5% by weight).

FORMULATION EXAMPLE 3

Preparation of Beverages

1. Preparation of health beverages 1000 mg of *Pistacia weinmannifolia* extract or fraction thereof prepared in Preparation Example 1 or 2

1000 mg of citric acid 100 g of oligosaccharide 2 of plum concentrate 1 g of taurine Adding purified water up to 900 ml The above ingredients were mixed according to a general health beverage preparation method, and heated with agitation at 85° C. for about 1 hour, and then the prepared solution was filtered to obtain in a sterilized 2L vessel, seal-sterilized and refrigeration-stored, and then used for the preparation of the health beverage composition of the present invention.

The above ratios illustrate a preferable example of mixing ingredients suitable for a favorite beverage; however, it can be modified arbitrarily according to regional and ethnic preference such as of the class of consumers or consumer country, the uses, etc.

2. Preparation of vegetable juice 5 g of the *Pistacia weinmannifolia* extract or fraction thereof prepared in Preparation Example 1 or 2 of the present invention was added to 1,000 mL of tomato or carrot juice to prepare vegetable juice for health improvement.

3. Preparation of fruit juice 1 g of the *Pistacia weinmannifolia* extract or fraction thereof prepared in Preparation Example 1 or 2 of the present invention was added to 1,000 mL of apple or grape juice to prepare fruit juice for health improvement.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

Effect of the Invention

A *Pistacia weinmannifolia* extract and a fraction thereof according to the present invention exhibit no cytotoxicity, inhibit production of inflammatory mediators, NO, IL-4, IL-5 and IL-13, and generation of reactive oxygen species in the airway, and remarkably induce reduction in the airway hyperresponsiveness and suppression of infiltration of inflammatory cells to the airway in an ovalbumin-induced asthma mouse model, and reduction of inflammatory cells in bronchoalveolar lavage fluid. Further, the *Pistacia weinmannifolia* extract and the fraction thereof of the present invention effectively inhibit secretion of immunoglobulins in the serum, mucus secretion in the airway, and infiltration of inflammatory cells to the lung tissue, thereby being safely used as a prophylactic or therapeutic agent for asthma.

What is claimed is:

1. A method of treating asthma, the method comprising:
   identifying a subject having asthma; and
   administering a pharmaceutical composition comprising an effective amount of *Pistacia weinmannifolia* (*Pistacia weinmannifolia* J. Poss. Ex Franch) extract or a solvent fraction thereof as an active ingredient to the subject.

2. The method of claim 1, wherein the extract is obtained by extracting *Pistacia weinmannifolia* with water, C1-C4 alcohol, or a mixture thereof.

3. The method of claim 1, wherein the extract is obtained by extracting *Pistacia weinmannifolia* with ethanol.

4. The method of claim 1, wherein the fraction is obtained by fractionating the extract of *Pistacia weinmannifolia* with water, C1-C4 alcohol, chloroform, ethyl acetate, hexane, butanol, or a mixture thereof.

5. The method of claim 1, wherein the extract or fraction thereof has the following activity:
   (a) inhibits NO (nitric oxide) production in microphages;
   (b) alleviates airway hyperresponsiveness;
   (c) reduces the number of eosinophils and inflammatory cells;
   (d) reduces serum IgE level;
   (e) inhibits generation of reactive oxygen species;
   (f) inhibits production of interleukin-4, interleukin-5, and interleukin-13;
   (g) inhibits inflammation and infiltration of inflammatory cells; or
   (h) inhibits mucus secretion in the airway.

6. A method of treating asthma, the method comprising:
   identifying a subject having asthma; and
   administering a health functional food comprising an effective amount of *Pistacia weinmannifolia* (*Pistacia weinmannifolia* J. Poss. Ex Franch) extract or a solvent fraction thereof as an active ingredient to the subject.

7. The method of claim 6, wherein the extract is obtained by extracting *Pistacia weinmannifolia* with water, C1-C4 alcohol, or a mixture thereof.

8. The method of claim 6, wherein the extract is obtained by extracting *Pistacia weinmannifolia* with ethanol.

9. The method of claim 6, wherein the fraction is obtained by fractionating the extract of *Pistacia weinmannifolia* with water, C1-C4 alcohol, chloroform, ethyl acetate, hexane, butanol, or a mixture thereof.

* * * * *